United States Patent [19]

Cannon, Jr.

[11] Patent Number: 4,493,539
[45] Date of Patent: Jan. 15, 1985

[54] METHOD AND APPARATUS FOR OBJECTIVE DETERMINATION OF VISUAL CONTRAST SENSITIVITY FUNCTIONS

[75] Inventor: Mark W. Cannon, Jr., Dayton, Ohio

[73] Assignee: The United States of America as represented by the Secretary of the Air Force, Washington, D.C.

[21] Appl. No.: 394,040

[22] Filed: Jun. 30, 1982

[51] Int. Cl.³ .......................... A61B 3/10; A61B 3/02
[52] U.S. Cl. .................................... 351/205; 351/211; 351/243
[58] Field of Search ............... 351/205, 211, 237, 239, 351/240, 241, 242, 243

[56] References Cited

U.S. PATENT DOCUMENTS 3,574,450  4/1971  White et al. ........................ 351/17
4,293,200  10/1981  Dobson et al. ..................... 351/36

OTHER PUBLICATIONS

Campbell and Maffei, "Electrophysiological Evidence for the Existence of Orientation and Size Detectors in the Human Visual System," *J. of Physiology*, 1970, vol. 207, pp. 635-652.

Regan, *Evoked Potentials*, Chapman & Hull Ltd., 1972, pp. 217, 218, 222-224.

Harris, Atkinson and Braddick, "Visual Contrast Sensitivity of a 6-Month-Old Infant Measured by the Evoked Potential," *Nature* Dec. 9, 1976, vol. 264, pp. 570-571.

Tyler, Apkarian, Levi and Nakayama, "Rapid Assessment of Visual Function: An Electronic Sweep Technique for the Pattern Visual Evoked Potential," *Invest. Ophthelmol. Vis. Sci.* Jul., 1979, vol. 18/7, pp. 703-713.

Ginsburg, "Proposed New Vision Standards for the 1980's and Beyond: Contrast Sensitivity," AFAMRL--TR-80-121, Sep., 1981.

*Primary Examiner*—Rodney B. Bovernick
*Attorney, Agent, or Firm*—Donald J. Singer; John R. Flanagan

[57] ABSTRACT

A method and apparatus for objectively determining the visual contrast sensitivity function of a human subject involves subjecting the vision of the human subject to a plurality of sine wave gratings differing in spatial frequency and contrast levels. As the subject views the grating patterns on a video monitor, the brain wave activity of the subject is detected and steady state Fourier spectra of the activity are recorded. In each spectrum corresponding to a grating pattern of a particular spatial frequency, a visual evoked potential component may be distinguished from noise by adjusting the contrast level of the grating pattern. A contrast threshold used in deriving the visual contrast sensitivity function is identified for each grating pattern of a particular spatial frequency by pinpointing the contrast level at which the visual evoked potential component becomes indistinguishable from noise in the spectrum.

4 Claims, 4 Drawing Figures

METHOD AND APPARATUS FOR OBJECTIVE DETERMINATION OF VISUAL CONTRAST SENSITIVITY FUNCTIONS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to measurement of visual sensitivity of a human subject and, more particularly, is concerned with a method of determining the human subject's visual contrast sensitivity function by objectively measuring threshold contrast levels in the steady state visual evoked potential waveform from the oecipital cortex area of the subject's brain.

2. Description of the Prior Art

Over the past decade, a new method of testing vision has come into use in both the scientific and clinical communities. The method measures visual sensitivity, using targets called sine wave gratings, that are specified in terms of two variables: spatial frequency and contrast.

A sine wave grating pattern is a repeated sequence of light and dark bars that has a luminance profile, which varies sinusoidally about a mean luminance with distance. The width of one light and one dark bar of a grating pattern is one cycle, or the period of the grating pattern. The reciprocal of the period is the spatial frequency. Spatial frequency is expressed by the number of cycles of the grating pattern that occur over a particular distance, more commonly the cycles per unit of visual angle or per degree (cpd) which is dependent upon the viewing distance. The luminance difference of the light and dark bars determines the contrast of the grating pattern. The Michelson definition of contrast is most often used:

$$C = (L_{max} - L_{min})/(L_{max} + L_{min})$$

where $L_{max}$ and $L_{min}$ are the maximum and minimum luminances of the bars of the grating pattern. Examples of the sine wave grating patterns having low, medium, and high spatial frequencies at low and high contrasts are shown in FIG. 1 on page 7 of Air Force Aerospace Medical Research Laboratory report No. AFAMRL-TR-80-121, dated September 1981.

Psychophysical experiments have shown that sine wave grating patterns are an appropriate stimulus for analyzing visual function. The periodic or repeated luminance patterns can be varied in contrast and spatial frequency, as shown in the aforementioned report, to determine the visual contrast threshold. If the contrast of a grating pattern is increased from below its visibility to where the grating is just seen, then the pattern is said to have reached threshold contrast. The reciprocal of the threshold contrast is called contrast sensitivity. Grating patterns of different spatial frequencies require different amounts of contrast to reach threshold for a particular human subject. Psychophysical experiments have measured visual contrast thresholds for sine wave grating patterns from 0.25 cpd of visual angle to 25 cpd.

In a typical psychophysical experiment for measuring contrast sensitivity, the human subject views a video screen and adjusts the contrast of a sine wave grating pattern displayed on the screen until the bars are just at the subject's threshold of visibility. The measurements are repeated for a number of different bar widths (spatial frequencies). The reciprocal of contrast threshold is plotted as a function of spatial frequency to create a psychophysically-determined contrast sensitivity function (CSF). A typical contrast sensitivity function is shown in FIG. 2 on page 8 of the aforementioned report. A subject's CSF has been shown to directly relate to how well that individual detects and identifies targets covering a wide range in size.

While the above-described psychophysical technique for determining a subject's CFS is satisfactory for research purposes, it relies on the cooperation and understanding of the subject and hence may not be suitable for routine usage in a clinical setting. Consequently, various researchers have attempted to devise a more objective approach to determination of a subject's CSF.

Toward this goal, visual evoked potentials (VEPs) of human subjects have been studied for use in determining their contrast thresholds. Steady state VEPs are electrical responses of the brain to a flickering pattern, picked up by surface electrodes placed on the subject's scalp over the occipital cortex. The responses are synchronized in frequency to the fundamental, or some harmonic of the, frequency at which the stimulus is flickering. Part of the problem of recording VEPs is that they are buried in the noise produced by other electrical activity in the brain that is not related to visual function. Therefore, some type of filtering or signal averaging is usually required to extract the VEP signal from the noise. Considerable efforts have been expended in the past to develop the VEP into a clinical and research tool for assessing pattern vision.

Campbell and Maffei (see "Electrophysiological Evidence for the Existence of Orientation and Size Detectors in the Human Visual System," *Journal of Physiology*, 1970, vol. 207, pp. 635–652) studied the relationship between steady state visual evoked potentials (VEP) and threshold contrast sensitivity for flickering sine wave gratings. They measured VEP amplitude over a range of contrasts and showed that regressions fitted to plots of the logarithm of contrast versus the VEP amplitude intersected the contrast axis near the psychophysically measured threshold at each spatial frequency. The only difficulty with this method is the inordinate amount of time required to obtain a subject's CSF.

Harris, Atkinson and Braddick (see "Visual Contrast Sensitivity of a 6-Month-Old Infant Measured by the Evoked Potential," *Nature*, Dec. 9, 1976, vol. 264, pp. 570–571) used the Campbell and Maffei method to determine thresholds for contrast in a situation where direct psychophysical methods were not possible, that is, in human infants. Tyler, Apkarian, Levi and Nakayama (see "Rapid Assessment of Visual Function: An Electronic Sweep Technique for the Pattern Visual Evoked Potential," *Invest. Ophthalmol. Vis. Sci.*, July 1979, vol. 18/7, pp. 703–713) developed an electronic spatial frequency sweep technique that assesses steady state VEPs more rapidly than the aforementioned threshold extrapolation method of Campbell and Maffei. However, Tyler et al admit that their technique does not produce contrast sensitivity functions and should only be used as an indicator of visual acuity.

While the above-mentioned approaches which utilize the VEPs of human subjects to arrive at an estimation of their CSFs are steps in the right direction, they still entail a considerable amount of time to be carried out, produce data of wide variability in individual responses, and require experienced personnel to perform the necessary regression analyses to arrive at the estimations of contrast thresholds. Therefore, a need exists for a more automated, faster approach to analyzing VEPs of human subjects and arriving at contrast threshold values of greater accuracy and repeatability.

SUMMARY OF THE INVENTION

The present invention provides a method and apparatus for objectively determining the visual contrast sensitivity functions of human subjects which is designed to satisfy the aforementioned needs. The unique features of the present invention are the concepts of determining a threshold contrast for the VEP signal component in a Fourier spectrum of brain activity for the human subject and the measurement of this threshold contrast by a numerical objective method that can be automated. By utilizing such concepts, the present invention solves the problem of relating the objective measurement of electrical activity in the brain to a well known subjective assessment of contrast sensitivity, the psychophysically-determined contrast sensitivity function. Furthermore, the VEPs of human subjects are analyzed in a manner which drastically reduces the variability heretofore experienced in individual responses.

Accordingly, the present invention provides a method and apparatus for objective determination of the contrast, at different spatial frequencies, for which the VEP signal component is just identifiable at a minimal detectable response level above the noise on the Fourier spectrum of electrical brain activity. These are VEP threshold contrasts and their reciprocal is the VEP contrast sensitivity. A graph of the VEP contrast sensitivity versus the spatial frequencies of the test provides the VEP contrast sensitivity function (VEP/CSF). Experiments conducted with this method and apparatus have shown that VEP/CSFs are directly related to psychophysical CSFs over a wide range of stimulus conditions. Furthermore, the present invention, using steady state VEPs, permits a VEP/CSF, defined at six spatial frequencies, to be generated in about eighteen minutes which is considerably quicker than can be achieved using the techniques of the aforementioned researchers.

DETAILED DESCRIPTION OF THE INVENTION

Figure 1:
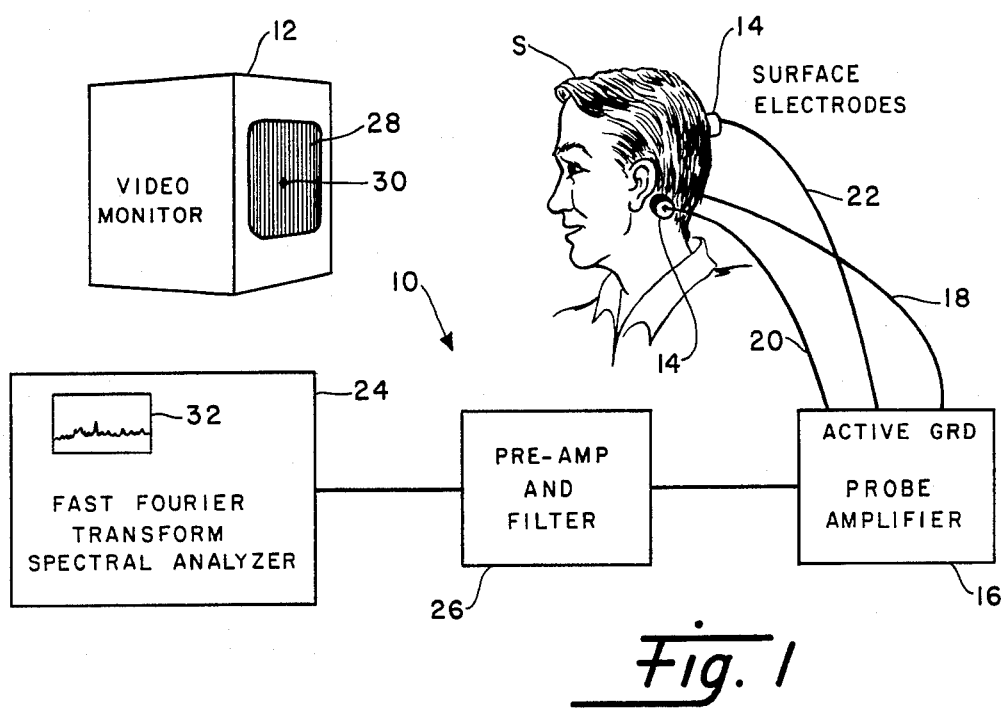
FIG. 1 is a schematic view of the apparatus of the present invention by which is carried out the method for objectively determining the visual contrast sensitivity functions of human subjects.

Referring now to the drawings, and more particularly to FIG. 1, there is schematically shown the preferred embodiment of the apparatus of the present invention, generally designated 10, connected to the head of a human subject S. The apparatus 10 detects the electrical brain activity of the subject S as the latter observes a flickering sine wave pattern on a video monitor or display 12. Further, the apparatus 10 is operable to analyze the Fourier spectrum of the steady state visual evoked potential (VEP) waveform contained in the electrical brain activity of the subject. Through manipulation of the apparatus in accordance with the steps of the method of the present invention, an objective measurement of the contrast thresholds, at various spatial frequencies, of the subject may be obtained by utilizing the subject's detected VEPs.

The apparatus 10 utilizes the video monitor 12 and three electrodes 14 (only two of which can be seen in FIG. 1) which are attached to the subject's scalp over the visual cortex of the brain. As mentioned before, the stimulus used in the present invention is a sine wave grating pattern which is adjustable in contrast and spatial frequency. Neither the method of pattern stimulus generation nor the method of attaching electrodes are per se original to the present invention. These features may be found in a treatise by David Regan, entitled *Evoked Potentials* (Chapman & Hull, Ltd., London, 1972), and for that reason are only treated schematically herein. The video monitor 12 may be one available from Joyce Electronics. The three electrodes may be Beckman surface electrodes which are attached to the head of the subject S, according to the ten-twenty electrode system discussed in the Regan treatise, at the locations of the Oz position and the left and right mastoids.

The apparatus 10 also includes a probe amplifier 16 to which the electrodes 14 are connected by leads 18, 20 and 22. A ground terminal (GRD) to the amplifier 16 is connected by lead 18 to the electrode (not shown) attached to the right mastoid location of the subject's scalp, while the active terminals of the amplifier 16 are connected by leads 20, 22 to the electrodes 14 at the two other scalp locations. Further, the apparatus 10 includes a fast Fourier transform spectral analyzer 24 and a pre-amp and filter 26 interconnected between the amplifier 16 and analyzer 24. In an exemplary embodiment of the apparatus, the probe amplifier 16 may be a Grass HIZ Probe Model HIP511E, the pre-amp and filter 26 may be a Grass AC Pre-Amp Model P511J, and the analyzer 24 may be a Nicolet Scientific Corporation 446B Fast Fourier Transform Spectral Analyzer.

For carrying out the method of the subject invention, the pre-amp and filter 26 is set at a gain equal to 10,000 and a bandwidth of 1 Hz to 1 KHz. The important settings of the switches on the front panel of the spectral analyzer 24 are: sensitivity—100 mv.; input—A.C.; display horizontal scale—linear x1; display vertical scale—linear x16; cursor amplitude, units—V, and reference—1V; cursor type—Hz; frequency range—50 Hz; spectrum average—N=8; test—off; and A-weighting—off. With these settings the spectral analyzer 24 records data for approximately one minute and computes Fourier spectra for eight overlapping eight-second samples of data. The final spectrum is the average of these eight individual spectra.

In VEP recording experiments carried out using the apparatus at the above described settings, sine wave grating pattern stimuli 28 were displayed on the monitor 12 at a mean luminance of 100 cd/m². A small fixation spot, such as at 30 in FIG. 1, 3 mm in diameter was placed on the center of the monitor screen. Grating patterns were flickered in counterphase mode, at rates ranging from 3 Hz to 20 Hz. The counterphase flicker at FHz produced pattern reversal twice per cycle at a rate of 2F Hz.

A human subject S is seated at a distance of 140 cm from the screen of the monitor 12 such that the screen subtends an area seven degrees in width by five degrees in height at the subject's eyes. The subject views the grating pattern binocularly with natural pupils against a dark surround. During VEP recording, the experimenter controls the contrast level of the grating pattern by means of a stepped attenuator (not shown).

VEPs of the subject are detected between the electrodes located at Oz and the left mastoid on the subject's scalp, with the electrode at the right mastoid grounded. Impedance of the electrodes is maintained at less than 4K ohms. VEPs are amplified at a gain of 10,000 by component 26, with filter half amplitudes at 1 Hz and 1 KHz. The output of component 26 is fed to analyzer 24 which computed the VEP spectrum from 0 to 50 Hz for most recording sessions. All VEP records consist of an average of eight spectra, each computed from eight seconds of data. All spectra are stored on magnetic tape for further analysis.

The human subject S is instructed to look at the grating pattern in the vicinity of the fixation spot 30 in the middle of the monitor screen. A contrast is selected by the experimenter for the flickering sine wave grating pattern and a one minute recording is made of the brain response. As mentioned before, flicker rates may range from 3 Hz to 20 Hz. The accumulating spectral average may be viewed on a display 32 of the analyzer 24 as time passes.

Figure 2:
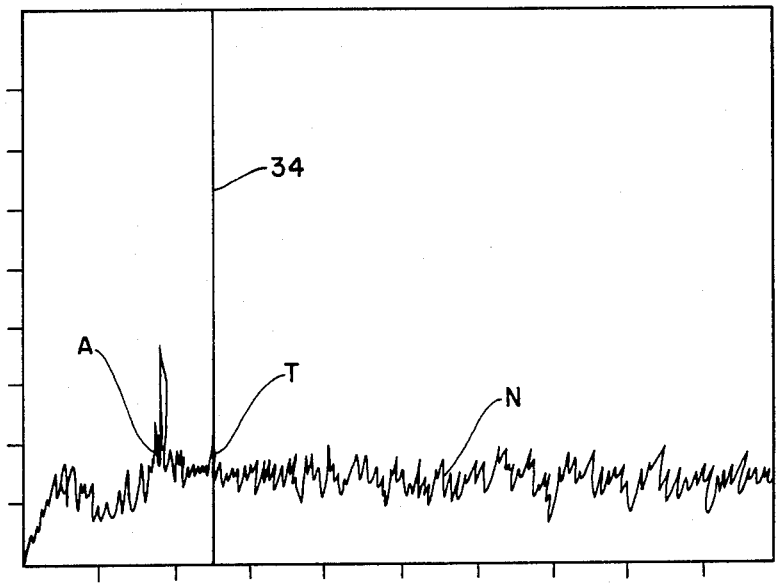
FIG. 2 is a replica of the steady state Fourier waveform spectrum seen on the screen of the spectral analyzer of the invention apparatus, with a cursor marking the sine wave pattern reversal rate at which a peak representing the contrast threshold will be identified.
Figure 3:
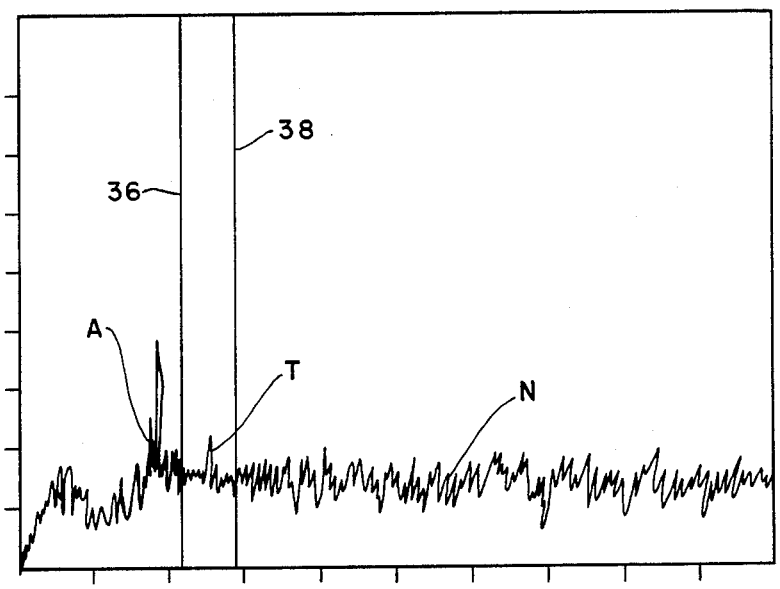
FIG. 3 is identical to FIG. 2 except that now left and right hand cursors are displayed at frequencies 1.5 Hz below and above the pattern reversal rate, respectively.

Referring to FIGS. 2 and 3, the components of the spectra usually seen are: (1) a wide band noise spectrum, N; (2) a broad peak from alpha activity at 10 Hz, A; and (3) a very sharp narrow peak at the pattern reversal rate (twice the flicker rate for the counterphase flickering), T. FIGS. 2 and 3 represent replicas of two photographs of the same spectra appearing on the analyzer display 32. In FIG. 2, a cursor 34 marks the pattern reversal rate. In FIG. 3, the left hand cursor 36 is set at a frequency 1.5 Hz below the pattern reversal rate, while the right hand cursor 38 is 1.5 Hz above the pattern reversal rate.

The voltage amplitude at the cursor 34, in one example, was 1.14 millivolts while the cumulative RMS voltage in the 3 Hz band between cursors 36 and 38 in the same example was 3.96 millivolts. The analyzer 24 computes this cumulative RMS voltage so as to yield an average voltage amplitude of 3.96 millivolts divided by the square root of twenty-four, or 0.808 millivolt (twenty-four is the number of frequency components within the 3 Hz band between the cursors; at each frequency component the voltage amplitude is measured and used in the computation of the RMS voltage, in this case, resulting in 3.96 millivolts). The signal-to-noise (S/N) ratio in this 3 Hz band is then 1.14 millivolts divided by 0.808 millivolts, or 1.41. Since a threshold criterion of 1.25 had been preestablished based on analyziing hundreds of records, it is apparent that this ratio (1.41) is greater than 1.25 and thus the VEP response is clearly suprathreshold.

If the initial response is greater than 1.25 (chosen as the decision criterion), the experimeter lowers the contrast by 2 or 4 dB and records another spectrum. At some contrast level, the S/N ratio will fall below 1.25 and the peak at the pattern reversal rate will be indistinguishable from the noise. On the other hand, if the initial contrast was too low, a S/N ratio less than or equal to 1.25 would result and the experimenter would search for threshold by increasing contrast. Threshold is defined as the contrast level 2 dB below the last contrast at which a S/N ratio greater than 1.25 was obtained.

Figure 4:
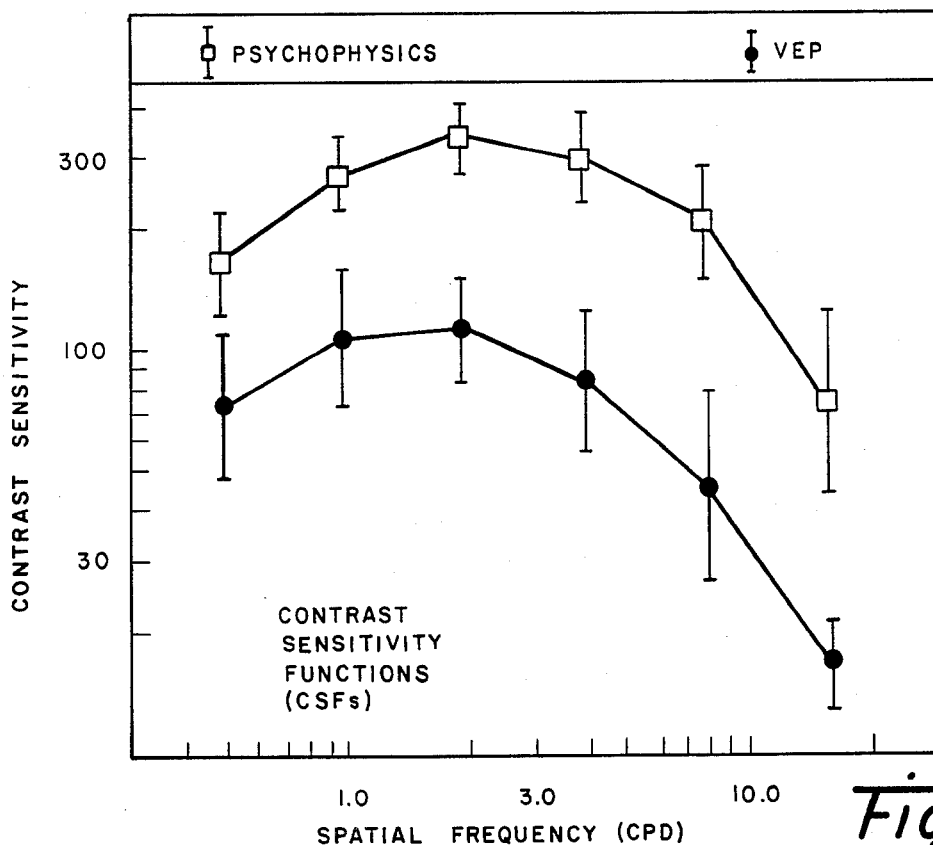
FIG. 4 is a graph illustrating the similarity in shape between the average CSF determined for twelve subjects using VEPs and the average psychophysical CSFs for the same twelve subjects.

This procedure is conducted for sine wave grating patterns at spatial frequencies of 0.5, 1, 2, 4, 8 and 16 cpd to determine a contrast threshold at each, and, since contrast sensitivity is the reciprocal of contrast threshold, to generate a contrast sensitivity function therefrom. It can be seen from the above discussion that the determination of the VEP contrast threshold is completely objective once a threshold criterion is established. Table 1 at the end of the description, which is self-explanatory, sets forth a representative sample record of data produced by the method of the present invention, as just described, which would be sufficient to graph a VEP/CSF curve similar to the one shown in FIG. 4. Once an experimenter has acquired some experience performing the method, locating a subject's VEP threshold can be done rapidly, requiring ordinarily only three to four data points at each spatial frequency.

In summary, a typical VEP response normally appears as a very narrow peak rising above a broad band noise spectrum. The minimal detectable response is limited by the average noise in the spectral region around the peak. A predetermined signal-to-noise ratio, defined as the spectral amplitude at the expected response frequency divided by the average amplitude across a 3 Hz wide spectral region centered on the stimulus and found equal to 1.25 in previous tests, is chosen as a decision criterion. However, one more condition is imposed to assure a real stimulus has been observed when S/N ratios between 1.25 and 1.3 are obtained. Contrast is increased by 2 or 4 dB, depending on the contrast level (2 dB for contrast less than 0.02), and another VEP record is recorded. If this ratio is less than 1.25, then the previous data point is rejected as denoting a response. Thus, threshold is defined as the contrast step (2 or 4 dB) below the last contrast at which a signal had been reliably reported.

Alternatively, an on-off (appearance-disappearance) mode of flickering the grating may be used instead of the counterphase (reversal) mode. On-off flicker at FHz will produce a grating pattern for one-half period and a blank screen at the average luminance for the other half period. Thus, the grating pattern appears once per cycle at a rate of FHz. The VEP component will be expected to appear at its greatest strength at the flicker frequency of FHz.

Experiments have shown that counterphase flicker VEP/CSF correlates equally well with psychophysical flicker or pattern CSFs. The on-off flicker VEP/CSF correlates highly with the psychophysical pattern CSF, but not very well with the psychophysical flicker CSF. One can conclude that VEP threshold data averaged over a number of subjects are highly correlated with similarily averaged psychophysical pattern threshold data as a function of spatial frequency and flicker rate for both counterphase and on-off flicker. However, pattern threshold CSFs for counterphase flickering gratings are different from pattern threshold CSFs for on-off flicker. Thus, in relating VEPs to psychophysical CSF data, it is required that both be recorded under the same experimental conditions. Also, from FIG. 4 it will be observed that while the VEP/CSF has a similar shape to the psychophysical CSF, its corresponding contrast sensitivity values are ordinarily lower in magnitude by a factor of 3 to 4.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

TABLE I

| dB | | 32 | 36 | 40 | 44 | 48 | 50 | 52 | 54 | 56 | 58 |
|---|---|---|---|---|---|---|---|---|---|---|---|
| C.S. | | 6.62 | 10.52 | 16.66 | 26.31 | 41.66 | 52.63 | 66.66 | 83.33 | 111.11 | |
| SPATIAL FREQ CPD | .5 | | | | (1) 1.68 | (2) 1.93 | (3) *1.15 | | | | |
| | 1 | | | | | (1) 1.79 | (3) 1.86 | (2) 1.33 (4) 1.57 | (5) *1.07 | | |
| | 2 | | | | (1) 1.15 | (4) 1.27 | (2) 1.30 | (3) *1.13 | | | |
| | 4 | | | | | (1) 2.26 | (3) 2.02 | (2) 1.06 (4) 1.58 | (5) 1.26 | (6) 1.30 | (7) *0.88 |
| | 8 | | | (2) 1.49 | (3) 1.62 | (1) *1.08 (4) 0.87 | | | | | |
| | 16 | (2) 1.32 | (1) 1.32 | (3) *1.02 | | | | | | | |

*Identifies contrast threshold where average S/N ratio first decreases below 1.25.
(.)—Numbers in parentheses indicate the sequence in which contrast of a grating pattern at particular spatial frequency was adjusted.
C.S. is contrast sensitivity.

Having thus described the invention, what is claimed is:

1. A method for objectively determining a visual contrast sensitivity function of a human subject, comprising the steps of:
   (a) subjecting the vision of a human subject to a plurality of flickering sine wave grating patterns differing in spatial frequency and contrast levels;
   (b) detecting brain wave activity of the human subject during viewing of said patterns and recording the steady state Fourier spectra of said activity;
   (c) distinguishing a visual evoked potential component from noise contained in each spectrum corresponding to a grating pattern of a particular spatial frequency; and
   (d) identifying a contrast threshold for each grating pattern of a particular spatial frequency corresponding to the contrast level at which said visual evoked potential component becomes indistinguishable from the noise of said spectrum, whereby the inverse of each contrast threshold may be plotted against the corresponding spatial frequency of said each grating pattern to yield the visual contrast sensitivity function of the human subject.

2. A method of objectively determining the visual contrast sensitivity function as recited in claim 1, wherein said identifying step includes:
   defining a signal-to-noise ratio as a decision criterion; and
   comparing to said decision criterion the signal-to-noise ratio for said visual evoked potential component of each spectrum corresponding to a grating pattern of a particular spatial frequency in order to identify said contrast threshold, said threshold being the contrast level at which the corresponding signal-to-noise ratio of said visual evoked potential component to noise has decreased in value below said decision criterion.

3. A method for objectively determining a visual contrast sensitivity function of a human subject, comprising the steps of:
   (a) subjecting the vision of the human subject to a sine wave grating pattern being flickered at a predetermined rate;
   (b) detecting and recording a steady state Fourier spectrum of brain wave activity of the human subject;
   (c) distinguishing a visual evoked potential component of said recorded spectrum from noise contained therein;
   (d) adjusting said grating pattern through a plurality of spatial frequencies;
   (e) adjusting said grating pattern in contrast level at each spatial frequency; and
   (f) identifying a contrast threshold of each grating pattern of a particular spatial frequency corresponding to the contrast level at which said visual evoked potential component of said spectrum becomes indistinguishable from the noise therein, whereby the inverse of each contrast threshold may be plotted against its corresponding spatial frequency to yield the visual contrast sensitivity function of the human subject.

4. Apparatus for objectively determining a visual contrast sensitivity function of a human subject, comprising:
   (a) a video monitor for generating a sine wave grating pattern being flickered at a predetermined rate;
   (b) means for detecting and recording a steady state Fourier spectrum of the brain wave activity of the human subject;

(c) means for adjusting said grating pattern through a plurality of spatial frequencies; and
(d) means for adjusting said grating pattern in contrast level at each spatial frequency in order to distinguish a visual evoked potential component of each recorded spectrum from noise contained therein and to identify a contrast threshold of each grating pattern of a particular spatial frequency corresponding to the contrast level at which said visual evoked potential component of said spectrum becomes indistinguishable from the noise therein, whereby the inverse of each contrast threshold may be plotted against its corresponding spatial frequency to yield the visual contrast sensitivity function of the human subject.

* * * * *